(12) United States Patent
Carlson et al.

(10) Patent No.: US 6,261,240 B1
(45) Date of Patent: Jul. 17, 2001

(54) METHOD AND APPARATUS FOR SENTINEL NODE BIOPSIES

(76) Inventors: Kara L. Carlson, 2710 107th Ave. SE., Bellevue, WA (US) 98004; Steve Abedon, 12040 NE. 128th St., Kirkland, WA (US) 98034

(*) Notice: Subject to any disclaimer, the term of this patent is extended or adjusted under 35 U.S.C. 154(b) by 0 days.

(21) Appl. No.: 09/443,757

(22) Filed: Nov. 22, 1999

(51) Int. Cl.7 .................................................. A61B 10/00
(52) U.S. Cl. ............................................................ 600/562
(58) Field of Search ............................ 600/566, 567, 600/578, 562, 585, 581, 582; 606/185

(56) References Cited

U.S. PATENT DOCUMENTS

| | | |
|---|---|---|
| 5,236,417 | 8/1993 | Wallis . |
| 5,320,110 * | 6/1994 | Wang ..................................... 600/566 |
| 5,353,804 | 10/1994 | Kornberg et al. . |
| 5,556,410 * | 9/1996 | Mittermeir et al. ................. 606/185 |
| 5,732,704 | 3/1998 | Thurston et al. . |

* cited by examiner

Primary Examiner—Eric F. Winakur
Assistant Examiner—Brian Szmal
(74) Attorney, Agent, or Firm—James C. Nemmers; Douglas J. Stilwell

(57) ABSTRACT

The present invention relates to an improved sentinel lymph node localization wire for use in breast cancer patients undergoing nodal staging. A hollow wire having an anchoring hook at the distal end is inserted into the breast tissue through a loading needle. The anchoring hook, through spring action upon release from the loading needle, is embedded in the breast tissue near the location of cancerous cells. The loading needle is then removed and radioactive material may be injected into the tissue through perforations in the localization wire without leaving the needle in the patient or without reinserting the needle. A syringe attachment may be affixed to the proximal end of the hollow wire to facilitate the injection of radioactive material and blue dye for localizing the sentinel lymph node.

19 Claims, 1 Drawing Sheet

METHOD AND APPARATUS FOR SENTINEL NODE BIOPSIES

BACKGROUND OF THE INVENTION

This invention is an improvement upon sentinel node localization systems. One of the latest developments in the staging of breast cancer is the sentinel lymph node biopsy. The status of the regional lymph nodes in the axilla (armpit) are one of the most powerful predictors of the survival of women with invasive breast cancer. The current standard of care for women with invasive breast cancer is the surgical removal of approximately two-thirds of the axillary lymph nodes for tumor staging. Most breast cancer patients, fortunately, have no spread of cancer to the lymph nodes. However, they endure the morbidity of the axillary lymph node dissection. Complications of an axillary lymph node dissection include arm edema (swelling), numbness and pain in the arm and axilla, and increased costs due to longer hospitalization.

The concept of the sentinel lymph node biopsy is to sample the first draining lymph node (the "sentinel node") nearest the site of the patient's breast cancer. If there is no evidence of tumor spread, then the patient does not have to undergo an axillary lymph node dissection. The procedure involves injecting radioactive material around the site of the cancerous tumor in the breast. This procedure typically is done in a radiology/nuclear medical department followed by transportation of the patient to an operating room where a surgeon uses a hand held gamma probe (camera) to localize the area of greatest radioactivity in the draining lymph nodes. The surgeon will also inject blue dye around the cancerous site and perform a lymphangiogram to aid in the identification of the sentinel lymph node.

If the patient has a palpable breast cancer, then the radioactive material and blue dye can be injected by palpation. If, however, the cancerous tumor in the breast cannot be felt, a localization wire must be placed prior to the injection of radioactive material. This procedure entails placing a needle into the tumor while the breast is in compression (similar to a mammogram), and deploying a localization wire with a distal hook (to secure it into the breast) through the needle and into the breast.

For a routine surgical biopsy/lumpectomy, the needle is slowly withdrawn out of the breast leaving the localization wire in place localizing the breast cancer site. However, in order to inject the radioactive material and blue dye for the sentinel lymph node procedure, the needle must stay in place and not be removed. A disadvantage of leaving the needle in place is that the breast cannot be massaged following placement of the radioactive material and blue dye to enhance the uptake of injected material into the breast lymphatics. It also places the breast at greater risk of injury while the patient is being transported, for example, from a radiology department to an operating room. There is therefore a need for an improved procedure that will eliminate these disadvantages of the presently employed sentinel lymph node procedure.

SUMMARY OF THE INVENTION

The present invention is an improved system for sentinel lymph node localization. The present invention simplifies and enhances the safety of the standard sentinel node biopsy procedure by allowing placement of radioactive material and blue dye through a hollow localization wire. This eliminates the requirement that a needle stay in place for these phases of the biopsy procedure. The hollow wire is deployed through a needle and anchored in the breast similar to a regular wire localization procedure. After the needle is withdrawn, and with the hollow wire in place in the breast, a syringe receptor, such as a rotating hemostatic valve, is threaded into the proximal end of the wire to allow injection of the radioactive material and blue dye.

DESCRIPTION OF THE PREFERRED EMBODIMENT OF THE INVENTION

Figure 1:
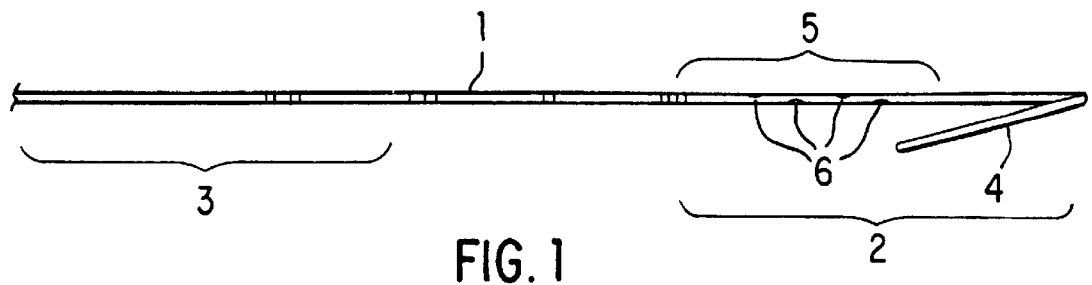
FIG. 1 is side elevational view of a hollow localization wire having a perforated region and an end hook.
Figure 2:
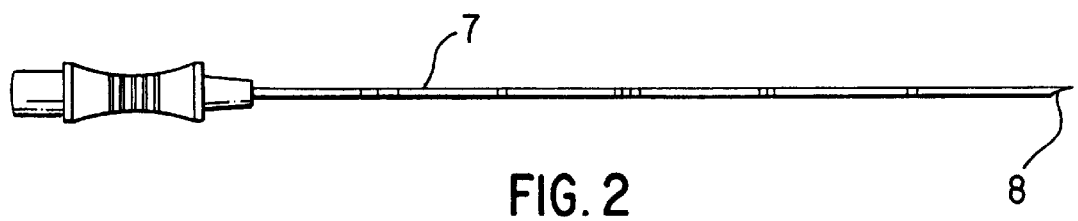
FIG. 2 is a side elevational view of a hollow localization wire loading needle.
Figure 3:
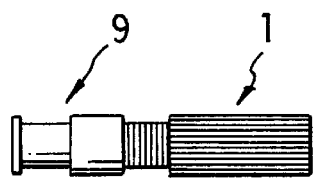
FIG. 3 is a detailed view of a Leur lock threaded into a hollow localization wire end.

FIG. 1 illustrates a hollow localization wire 1 constructed according to the principles of the invention. The invention is described in connection with a sentinel lymph node biopsy procedure of a patient's breast, but it will be understood that the method and device of the invention may be useful in other procedures. The localization wire 1 has a distal end 2 and at least one proximal end 3. The distal end 2 is placed at the location of targeted cancerous cells. A hook 4 integral with the hollow localization wire 1 at its distal end 2 is used to anchor the hollow localization wire 1 near the target cancerous cells in the patient's breast. A portion 5 of the hollow localization wire 1, generally near the distal end 2, contains perforations 6 which allow the release of radioactive material, blue dye, or other substances flowing through the hollow wire 1 into the tissues surrounding the patient's breast cancer. In the preferred embodiment, the hollow localization wire is carried by a loading needle 7 for insertion into the targeted area of the patient's breast. When the hollow localization wire 1 is inserted through the loading needle 7, the distal end hook 4 will be compressed and held in a constrained position generally parallel with the hollow localization wire 1. The distal end hook 4 will flex from its constrained position to an extended, anchoring position through spring action when released from the loading needle end 8. FIG. 1 illustrates this anchoring position.

After the hollow localization wire is anchored near the cancerous cells in the targeted area of the patient's breast, the loading needle 7 may be removed. After removal of the loading needle 7, the proximal end 3 of the hollow localization wire 1 remains exposed, outside of the patient's skin. A rotating hemostatic valve, such as syringe receptor 9, is affixed to the hollow localization wire proximal end 3. In the presently preferred embodiment, we have illustrated use of a Leur lock as the syringe receptor 9. The syringe receptor 9 is threaded into the proximal end 3 of the hollow localization wire 1 and is tightened or screwed into place.

Figure 4:
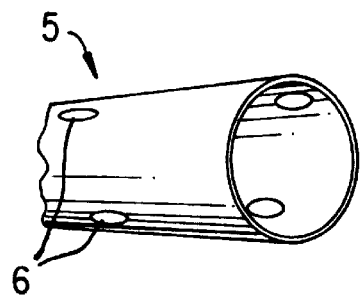
FIG. 4 is a perspective view of a portion of the perforated region of a hollow localization wire.

FIG. 4 illustrates a detailed view of the perforated region 5 of the hollow localization wire 1 in the presently preferred embodiment. The perforated region 5 contains four openings such as perforations 6 in the wall of the hollow localization wire 1. These perforations 6 are located in a generally spiral pattern, each separated by 90 degrees of rotation. The invention may contain one or a plurality of perforations 6.

The preferred loading needle 8 is a 19 gauge needle with a length of 5, 7, or 9 cm. The preferred hollow localization wire 1 is a 0.035 inch, hollow, extruded wire with a length of 11, 15, or 20 cm. These lengths, gauges, and diameters are those currently preferred for use with the presently practiced procedure of sentinel lymph node localization in breast cancer patients. However, the invention is not limited to these specific dimensions. The present invention is described with specific reference to hollow localization wires for use in sentinel node localization in breast cancer patients and body types vary widely. Moreover, because the present invention can also be used in applications other than breast biopsy that require the localization of target regions and injection of tracers or other materials, sizes appropriate to the specific application, and the number and arrangement of perforations will necessarily vary from the disclosed preferred embodiment.

The preferred material for the components of the invention is any material suitable for temporary placement in the human body.

Having thus described the invention in connection with the preferred embodiments thereof, it will be evident to those skilled in the art that various revisions can be made to the preferred embodiments described herein without departing from the spirit and scope of the invention. It is our intention, however, that all such revisions and modifications that are evident to those skilled in the art will be included within the scope of the following claims.

What is claimed is as follows:

1. An anchorable hollow wire for use in injecting fluids into tissue of a patient, the wire comprising:

an elongated hollow shaft through which fluids can be injected and having a proximal end and a distal end; and a hook combined with the hollow shaft at the hollow shaft distal end;

said shaft having at least one opening generally near the distal end to provide for discharge of fluids from the shaft into the tissue of a patient.

2. The anchorable hollow wire of claim 1 wherein:

the hook is movable from a constrained position to an anchoring position.

3. The anchorable hollow wire of claim 2 wherein:

the hook is movable through spring action from its flexed, constrained position generally parallel with the hollow shaft to its extended, anchoring position wherein the angle formed between the hook and the hollow shaft is greater than the angle formed when the hook is in the flexed position.

4. A hollow sentinel node localization wire comprising:

a hollow shaft having at least one wall, at least one proximal end, and a distal end;

said wall having a perforated region defining at least one discharge opening located generally near the distal end; and a hook integral with the shaft generally near the distal end.

5. The hollow sentinel node localization wire of claim 4 wherein:

the perforated region defines a plurality of discharge openings located generally near the distal end and distributed generally along the shaft.

6. The hollow sentinel node localization wire of claim 4 wherein:

the perforated region defines a plurality of discharge openings located generally near the distal end and distributed along the shaft in a generally spiral pattern at locations separated by a rotation of about 90 degrees.

7. The hollow localization wire of claim 4 further comprising:

a removable loading needle having a wall that forms an opening, said opening adapted to receive the hollow localization wire.

8. The hollow localization wire of claim 4 further comprising:

a syringe receptor engaging the hollow wire near the proximal end.

9. The hollow localization wire of claim 8 wherein:

the syringe receptor comprises a Leur lock.

10. The hollow localization wire of claim 8 wherein:

the syringe receptor comprises a rotating hemostatic valve.

11. The hollow localization wire of claim 8 wherein:

the syringe receptor is removable.

12. The hollow localization wire of claim 8 wherein:

the hook is movable from a constrained position to an anchoring position.

13. The hollow localization wire of claim 8 wherein:

the hook is movable through spring action from its flexed, constrained position generally parallel with the hollow shaft to its extended, anchoring position wherein the angle formed between the hook and the hollow shaft is greater than the angle formed when the hook is in the flexed position.

14. A method of safely injecting a tracer into a patient for performing a sentinel node biopsy comprising the steps of:

inserting a hollow localization wire into a patient;

anchoring the hollow localization wire in the patient; and injecting at least one tracer through the hollow localization wire.

15. The method of claim 14 safely injecting a tracer into a patient for performing a sentinel lymph node biopsy comprising the steps of:

inserting a hollow localization wire into a patient through a loading needle;

anchoring the hollow localization wire in the patient;

removing the loading needle from the patient; and injecting at least one tracer through the hollow localization wire.

16. The method of claim 14 further comprising the step of:

anchoring the hollow localization wire in the patient with a spring action hook that moves from a constrained position to an anchoring position upon release from the loading needle.

17. The method of claim 14 wherein:

at least one injected tracer is a radioactive tracer.

18. The method of claim 14 wherein:

at least one injected tracer is a dye.

19. The method of claim 14 further comprising the steps of:

affixing a syringe attachment to the hollow localization wire;

injecting at least one tracer through the syringe attachment.

* * * * *